United States Patent

Vassiliadis et al.

Patent Number: 5,310,344
Date of Patent: May 10, 1994

[54] DENTAL LASER SYSTEM

[76] Inventors: Arthur Vassiliadis, 707 Continental Cir. #412, Mountain View, Calif. 94040; Joseph W. Shaffer, 235 Vincent Dr., Mountain View, Calif. 94041; David J. Fullmer, 156 Rock Harbor La., Foster City, Calif. 94404; Michael H. Brewer, 8001 Pine Dr., Felton, Calif. 95018; David R. Hennings, 190 Welcome Rd., Newcastle, Calif. 95658; Terry D. Myers, 25334 Lyncastle, Farmington Hills, Mich. 48018; William D. Myers, 5855 Wingcroft Ct., Birmingham, Mich. 48010

[21] Appl. No.: 607,817
[22] Filed: Nov. 1, 1990
[51] Int. Cl.⁵ ............................ A61C 5/00
[52] U.S. Cl. .................. 433/215; 606/15; 606/16
[58] Field of Search .......... 433/215, 229; 606/14, 606/15, 16, 17

[56] References Cited

U.S. PATENT DOCUMENTS

| | | | |
|---|---|---|---|
| 4,362,057 | 12/1982 | Gottlieb et al. | 350/96.29 X |
| 4,521,194 | 6/1985 | Myers et al. | 433/215 |
| 4,583,539 | 4/1986 | Karlin et al. | 128/303.1 |
| 4,672,969 | 6/1987 | Dew | 606/16 X |
| 4,736,743 | 4/1988 | Daikuzono | 606/16 X |
| 4,747,660 | 5/1988 | Nishioka et al. | 606/14 X |
| 4,784,135 | 11/1988 | Blum et al. | 128/395 X |
| 4,794,619 | 12/1988 | Tregay | 350/96.29 X |
| 4,840,174 | 6/1989 | Gluckman | 606/16 X |
| 4,849,859 | 7/1989 | Nagasawa | 606/16 X |
| 4,852,567 | 8/1989 | Sinofsky | 606/15 X |
| 4,911,712 | 3/1990 | Harrington | 350/96.32 X |
| 4,917,084 | 4/1990 | Sinofsky | 606/15 X |
| 4,940,411 | 7/1990 | Vassiliadis et al. | 433/215 |
| 4,950,266 | 8/1990 | Sinofsky | 606/15 X |
| 5,030,217 | 7/1991 | Harrington | 606/14 |
| 5,118,293 | 6/1992 | Levy | 433/215 |

FOREIGN PATENT DOCUMENTS

| | | | |
|---|---|---|---|
| 0376148 | 7/1990 | European Pat. Off. | 433/215 |
| 2948580 | 6/1980 | Fed. Rep. of Germany | 606/16 |

Primary Examiner—Gene Mancene
Assistant Examiner—Nicholas D. Lucchesi
Attorney, Agent, or Firm—Gifford, Groh, Sprinkle, Patmore and Anderson

[57] ABSTRACT

A dental laser system is disclosed having an erbium doped YAG laser which is excited so that the YAG laser produces a plurality of laser pulses. A novel delivery system for the YAG laser is disclosed which includes an elongated sapphire strand which consists of a single crystal. The sapphire strand has a diameter between 10 and 1000 microns so that it maintains its flexibility and the sapphire strand is encased within a flexible protective coating. The sapphire strand is also essentially devoid of water content.

10 Claims, 1 Drawing Sheet

DENTAL LASER SYSTEM

BACKGROUND OF THE INVENTION

I. Field of the Invention

The present invention relates to a dental laser system and, more particularly, to a dental laser system using an erbium laser and a sapphire fiber strand for delivering the laser output to the treatment site in a dental application.

II. Description of the Prior Art

There are previously known dental laser systems which have been developed by the assignee of the present invention which utilize a pulsed YAG laser to perform various dental treatments in the mouth of the patient. These previously known lasers typically utilize a neodimium doped YAG laser.

With these previously known systems, the YAG laser is contained within a housing having a laser output port. In order to deliver the YAG laser output to the mouth of the patient, an elongated quartz fiber strand extends between the laser output port on the housing and a handpiece which is manipulated by the dentist. The quartz fiber strand has a small diameter, typically about 300 microns, and is flexible in use thereby allowing the dentist to manipulate the strand to the desired delivery site in the patient's mouth.

These previously known quartz fiber strands, however, have been unsuitable for use with an erbium doped YAG laser. More specifically, the erbium doped YAG laser, due to its wavelength, tends to break down and otherwise degregate the integrity of the quartz fiber so that the quartz fiber cannot be used with the erbium doped laser.

Although articulated arms with mirrors may be used to deliver the erbium doped laser output to the treatment site, such articulated arms have proven to be awkward, clumsy and therefore undesirable to use.

SUMMARY OF THE PRESENT INVENTION

The present invention provides a dental laser system for an erbium doped YAG laser which overcomes all of the above mentioned disadvantages of the previously known devices.

In brief, the dental laser system of the present invention comprises an erbium doped YAG laser and means for exciting the laser so that the laser produces a plurality of laser light pulses. Furthermore, an erbium doped YAG laser is particularly advantageous for dental applications since an erbium doped laser, due to its output, has proven to be particularly effective for removing both carious and non-carious enamel from teeth.

An elongated sapphire fiber strand has one end connected to the laser output port on the erbium doped YAG laser while a contact or non-contact handpiece is connected to the opposite end of the strand. The strand consists of a single crystal of sapphire and has a diameter between 10 and 1000 microns so that the strand retains its flexibility.

A protective sheathing is also provided around the sapphire fiber strand in order to protect the strand from damage and loss of light. The sheathing can be constructed of any conventional material but preferably has a lower index of light refraction than the sapphire strand so that any laser light contacting the sheathing is reflected back into the strand.

In an alternative embodiment of the invention, an elongated flexible tube having a light refractive interior surface is used to deliver the erbium laser output from the layer output port to the treatment site.

BRIEF DESCRIPTION OF THE DRAWING

A better understanding of the present invention will be had upon reference to the following detailed description, when read in conjunction with the accompanying drawing, wherein like reference characters refer to like parts throughout the several views, and in which.

DETAILED DESCRIPTION OF PREFERRED EMBODIMENTS OF THE PRESENT INVENTION

Figure 1:
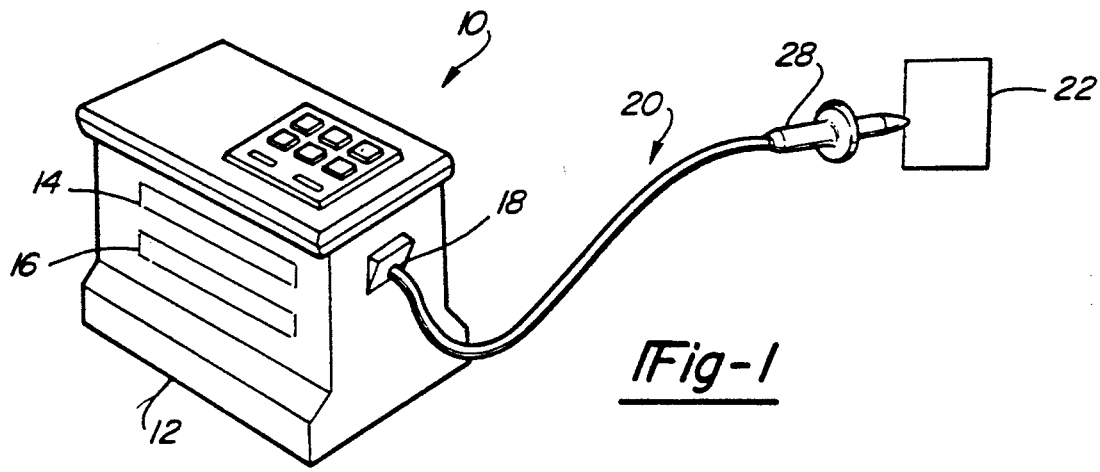
FIG. 1 is a perspective view illustrating a preferred embodiment of the present invention.

With reference first to FIG. 1, a preferred embodiment of the dental laser system 10 of the present invention is thereshown and comprises a housing 12 containing an erbium doped YAG laser 14. Conventional means 16 are also contained within the housing 12 for exciting the laser 14 so that the laser produces a plurality of output pulses to an output port 18 on the exterior of the housing 12.

The dental laser system also includes a delivery means 20 which delivers the output from the laser 14 from the output port 18 to a treatment site 22 in the mouth. Furthermore, the erbium laser 14, due to its wavelength, is particularly effective for removing enamel from teeth of the patient.

Figure 2:
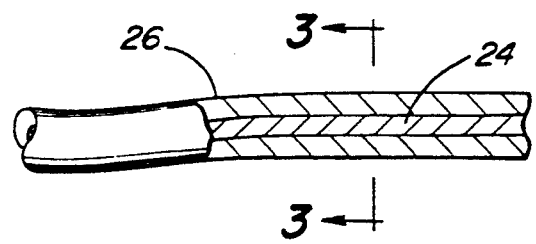
FIG. 2 is a fragmentary longitudinal sectional view illustrating a portion of the preferred embodiment of the present invention and enlarged for clarity.
Figure 3:
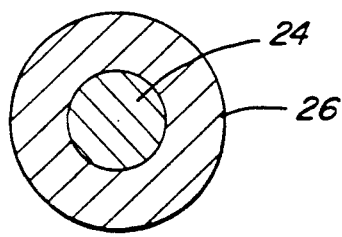
FIG. 3 is a cross-sectional view taken substantially along line 3-3 in FIG. 2.

With reference now to FIGS. 1-3, the delivery system 20 comprises an elongated sapphire fiber strand 24 which consists of a single crystal and is of sufficient length so that the strand 24 extends from the port 18 to the treatment site 22. The strand 24 has a diameter between 10 microns and 1000 microns and preferably between 200 and 600 microns, and thus retains its flexibility. Furthermore, the strand 24 is essentially devoid of any water content since such water content adversely reacts with the erbium laser output.

As best shown in FIGS. 2 and 3, a protective sheathing 26 is provided around the sapphire strand 24 substantially entirely along its length. The sheathing 26 may be constructed of any conventional material, such as plastic, quartz or glass, and protects the strand 24 both from damage, as well as light leakage. Furthermore, the sheathing 26 has a lower index of light refraction than the strand 24 so that any light which contacts the interior surface of the sheathing 26 is reflected back into the strand 24 for delivery to the treatment site 22.

From the foregoing, it can be seen that the present invention provides a dental laser system for an erbium doped YAG laser having a flexible delivery system 20 which facilitates the delivery of the laser output to the treatment site 22. Furthermore, a handpiece 28 (FIG. 1) is preferably attached at one end of the delivery means 20 in order to facilitate the manipulation of the delivery means 20.

Figure 5:
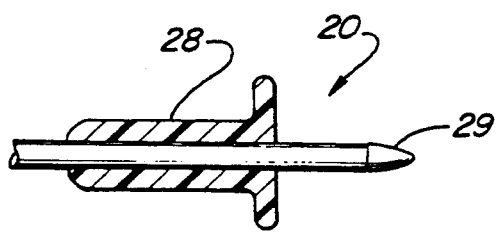
FIG. 5 is a side view illustrating a modification of the invention.

The erbium doped laser has proven particularly effective for removing hard material, such as dental enamel and decay, as well as in endodontic and peridontal applications. However, the erbium doped laser is also effective to remove soft tissue and, when soft tissue is removed, a contact tip 29 (FIG. 5) may be used at the end of the strand 24. The contact tip is constructed of a high temperature material which heats up in use. Alternatively, the distal end of the sapphire fiber can be used to make direct contact with the target area.

Figure 4:
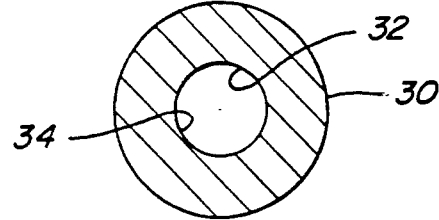
FIG. 4 is a cross-sectional view similar to FIG. 3 but illustrating a second preferred embodiment of the present invention.

With reference now to FIG. 4, a second preferred embodiment of the present invention is thereshown in which the delivery system 20 comprises an elongated tube 30 which is constructed of any suitable flexible material, such as plastic. The tube 30 has an internal bore 32 having a diameter between 10 and 5000 microns. Furthermore, the internal bore 32 has a reflective covering 34 provided along its entire length.

In practice, the tube 30 is connected to the output port 18 (FIG. 1) while the handpiece 28 is connected to the opposite end of the tube 30. The output from the laser 14 travels through the internal bore 32 of the tube 30 from the output port 18 to the delivery site 22. Furthermore, any contact between the laser output and the internal bore of the tube 30 is reflected by the coating 34 so that the laser output is contained within the tube bore 32.

As is well known, the laser output from the erbium laser is invisible. Consequently, an aiming beam, such as a continuous wave helium-neon laser, is also transmitted through either the strand 24 or tube 30.

Having described our invention, however, many modifications thereto will become apparent to those skilled in the art to which it pertains without deviation from the spirit of the invention as defined by the scope of the appended claims.

We claim:

1. A dental laser system comprising:
   an erbium doped YAG laser for dental treatment applications,
   means for exciting said laser so that said laser produces a plurality of laser light pulses,
   means for delivering said light pulses to a site in a mouth of a patient remote from said laser, said delivery means comprising a sapphire fiber strand, said sapphire fiber strand consisting of a single crystal having a solid cross-sectional shape.

2. The invention as defined in claim 1 wherein said fiber strand is essentially devoid of water.

3. The invention as defined in claim 1 wherein said strand has a diameter between about 10 microns and 1000 microns.

4. The invention as defined in claim 1 and comprising a protective sheathing surrounding and covering substantially the entire length of said strand.

5. The invention as defined in claim 4 wherein said sheathing is constructed of plastic.

6. The invention as defined in claim 4 wherein said sheathing is constructed of quartz.

7. The invention as defined in claim 4 wherein said sheathing is constructed of glass.

8. The invention as defined in claim 4 wherein said sheathing has an index of light refraction lower than said strand.

9. The invention as defined in claim 1 wherein said strand has a diameter between 200 microns and 600 microns.

10. The invention as defined in claim 1 and comprising a contact tip attached to a distal end of said strand.

* * * * *